US006673863B2

(12) United States Patent
Travkina et al.

(10) Patent No.: US 6,673,863 B2
(45) Date of Patent: Jan. 6, 2004

(54) GEL COMPOSITION AND METHODS OF USE

(75) Inventors: Irina Travkina, River Edge, NJ (US);
Lisa Lamberty, Hawthorne, NJ (US);
Harold Pahlck, Waldwick, NJ (US)

(73) Assignee: Avon Products, Inc., Suffern, NY (US)

( * ) Notice: Subject to any disclaimer, the term of this patent is extended or adjusted under 35 U.S.C. 154(b) by 23 days.

(21) Appl. No.: 10/023,029

(22) Filed: Dec. 17, 2001

(65) Prior Publication Data

US 2003/0114572 A1 Jun. 19, 2003

(51) Int. Cl.$^7$ .............................. C08J 3/00; C08K 3/54; C08L 57/02; A61K 51/00; A61K 9/00
(52) U.S. Cl. ....................... 524/492; 424/1.29; 424/400; 424/401; 424/417; 424/421; 424/65; 523/105; 524/493; 524/494; 524/499
(58) Field of Search ................ 424/1.29, 400, 424/401, 417, 421, 65; 523/105; 524/492, 493, 494, 499

(56) References Cited

U.S. PATENT DOCUMENTS 5,679,361 A    10/1997  Pradier et al.
5,976,560 A    11/1999  Han et al.
2002/0106385 A1  8/2002  Vatter et al. ................. 424/401

OTHER PUBLICATIONS

Patent Application Publication US 2002/0106385, Vatter et al., Aug. 2002.*

International Search Report, PCT Patent Application No. PCT/US02/34893, Filed Oct. 31, 2002.

* cited by examiner

*Primary Examiner*—Patrick D. Niland
(74) *Attorney, Agent, or Firm*—Ohlandt, Greeley, Ruggiero & Perle

(57) ABSTRACT

There is provided a gel composition having a silica powder and a non-volatile compound. The silica powder particles are spherical and porous. The silica powder has a specific gravity about 0.09 to about 0.6, and is present in an amount about 10 wt % to about 50 wt %. The non-volatile compound is present from about 35 wt % to about 90 wt %. The composition has less than about 5 wt % water. There is also provided a method for imparting a powdery feel to the skin, and a method for treating a cosmetic or medical condition of the skin, nail/cuticle, lips or hair.

26 Claims, No Drawings

GEL COMPOSITION AND METHODS OF USE

BACKGROUND OF THE INVENTION

1. Field of the Invention

The present invention relates to a substantially anhydrous gel composition that imparts a powdery, non-oily feel to the skin. The present invention also relates to a gel composition useful as a vehicle or base for cosmetic, skin care, and medicinal ingredients.

2. Description of the Prior Art

Gel compositions are employed in the cosmetic and skin care industries to impart or deliver a variety of cosmetic and skin care ingredients to the skin. Gel compositions have proven desirable because they are easy to manufacture and can be formulated to be translucent or transparent.

A problem with employing gel compositions is that they sometimes impart an oily feel to the surface of the skin or leave a perceptible film-like residue. Another problem is that they frequently employ significant concentration of volatile organic compounds that may require explosion-proof equipment and/or special handling in the manufacturing process.

U.S. Pat. No. 5,679,361 relates to a make-up composition having a fatty phase and a pulverulent phase. The pulverulent phase has silica or thermoplastic microspheres with a specific gravity not exceeding 0.07. The fatty phase may be fatty oils of animal, vegetable, mineral or synthetic origin, as well as waxes. The fatty phase includes oils, such as hydrocarbon oils and silicone oils. There is no disclosure that the composition is in gel form, or that it imparts a powdery feel upon application to skin.

U.S. Pat. No. 5,976,560 relates to a replacement for petroleum jelly as a base for skin care products. The base has a vegetable oil and a fumed silica. There is no disclosure that the composition imparts a powdery feel upon application to skin.

Thus, there is still a need for a gel composition that imparts a powdery feel to the skin upon application. It is also desired to have a gel composition that is substantially free of volatile organic compounds. It would also be desirable to have a gel composition that is useful as a vehicle or base for cosmetic, skin care, and medicinal ingredients.

SUMMARY OF THE INVENTION

It is an object of the present invention to have a gel composition that imparts a powdery, non-oily feel to the skin upon application.

It is another object of the present invention to have a gel composition that is substantially free of volatile compounds.

It is still another object of the present invention to have a gel composition that is useful as a vehicle or base for cosmetic, skin care, and medicinal ingredients.

It is a further object of the present invention to have a gel composition that has less than about 5 wt % of a volatile compound.

It is still a further object of the present invention to have a gel composition that has less than about 5 wt % water.

These and other objects and advantages are achieved by a gel composition of the present invention. The gel composition has a silica powder and a non-volatile compound. The silica powder particles are spherical and porous. The silica powder has a specific gravity about 0.09 to about 0.6, and is present in an amount about 10 wt % to about 50 wt %. The non-volatile compound is present in an amount about 35 wt % to about 90 wt %.

The present invention also includes a cosmetic for application to the skin. The preferred cosmetic is a composition, preferably having a gel matrix, with a silica powder and a non-volatile hydrocarbon oil, and a color pigment. The present invention also provides a method for imparting a powdery feel to the skin that includes applying the composition to the skin. The present invention further provides a method for treating a cosmetic or medical condition of the skin, nail/cuticle, lips or hair that includes applying an amount of the composition to the affected area.

DETAILED DESCRIPTION OF THE INVENTION

It was found surprising that a composition, that is in a gel form in a container, could impart a pleasant, powdery feel to the skin upon application. It was also surprising that the gel composition could be formulated without a volatile organic compound. It was also surprising that such a gel composition could be used as a vehicle or base for cosmetic or skin care ingredients.

In the present invention, a silica powder and a non-volatile compound are processed to form a gel matrix that is spongy and soft to the touch. When applied to the skin, the matrix in the form of a composition imparts a powdery feel to the surface thereof, without any oily film residue.

The silica powder functions as a gelling agent in the composition to form a gel matrix with the non-volatile compound. The silica powder has particles that are spherical and porous.

The silica powder has a specific gravity of about 0.09 to about 0.6, preferably about 0.2 to about 0.5, and most preferably about 0.3 to about 0.4. The silica powder has an average particle size about 2 microns ($\mu$m) to about 20 $\mu$m, preferably about 3 $\mu$m to about 15 $\mu$m, and more preferably about 3 $\mu$m to about 5 $\mu$m. A most preferred average particle size is about 3 $\mu$m.

The silica powder preferably has an oil absorption about 100 to about 300 grams of oil, more preferably about 120 to about 170 grams of oil, and most preferably about 150 grams of oil, per 100 grams of silica.

The silica powder preferably has a specific surface area about 100 m$^2$ to about 1,000 m$^2$, more preferably about 600 m$^2$ to about 800 m$^2$, and most preferably about 700 m$^2$, per gram of silica powder. The silica powder is preferably non-fumed.

The silica powder is present in the gel composition in an amount about 10 percentage by weight or weight percent (wt %) to about 50 wt % of the total weight of the composition. Preferably, the silica powder is present in an amount about 15 wt % to about 45 wt %, and more preferably about 25 to about 35 wt %, of the total weight of the composition.

A non-volatile compound useful in the present composition is preferably one with a viscosity less than about 50 centistokes (cst) at 25° C., preferably less than about 30 cst, more preferably less than about 20 cst, and most preferably less than about 10 cst. Preferred non-volatile compounds include one or more non-volatile hydrocarbon compounds, particularly oil, such as hydrocarbon oil. Such hydrocarbon oils include, but are not limited to, squalane, liquid paraffin, $C_{12-15}$ alcohol benzoates, hydrogenated polyisobutene, and hydrogenated polydecene. Squalane is preferred.

The non-volatile compound is present in the composition in an amount about 35 wt % to about 90 wt % of the total weight of the composition. The non-volatile compound is preferably present in an amount about 40 wt % to about 70 wt %, and more preferably about 45 wt % to about 65 wt %, of the total weight of the composition.

The gel composition is substantially anhydrous or free of water. The composition preferably has less than about 5 wt % water. More preferably, the composition has less than about 1 wt % water based on the total weight of the composition. Most preferably, the composition is free of water.

A surprising, unexpected attribute of the present invention is its translucent/transparent appearance. The composition may further be colored with the addition of a pigment or colorant. The superiority in clarity of the base of the composition provides a finished product that is more true to the pigment/colorant shade.

The present composition may optionally include a non-aqueous vehicle in addition to the non-volatile compound. Suitable vehicles and/or vehicle components include, but are not limited to, one or more vegetable oils; esters such as octyl palmitate, isopropyl myristate and isopropyl palmitate; ethers such as dicapryl ether and dimethyl isosorbide; fatty alcohols such as cetyl alcohol, stearyl alcohol and behenyl alcohol; isoparaffins such as isooctane, isododecane and isohexadecane; silicone oils such as dimethicone and polysiloxane; hydrocarbon oils such as petrolatum, isoeicosane and polyisobutene; polyols such as propylene glycol, glycerin, butylene glycol, pentylene glycol and hexylene glycol; or any combinations of the foregoing.

The composition may also have a volatile organic compound, but preferably has less than about 5 wt %, and more preferably less than about 1 wt %, of one or more volatile compounds, based on the total weight of the composition. Most preferably, the composition is substantially free of volatile compounds. Volatile compounds as defined herein have a vapor pressure of greater than about 0.01 Kpa at 25° C. and atmospheric pressure.

Optionally, the present composition may have one or more of the following additional ingredients: anesthetics, anti-allergenics, antifungals, antimicrobials, anti-inflammatories, antiseptics, emulsifiers (either anionic or nonionic), botanical extracts, chelating agents, colorants, depigmenting agents, emollients, exfollients, film formers, fragrances, humectants, insect repellents, lubricants, moisturizers, pharmaceutical agents, preservatives, skin protectants, skin penetration enhancers, stabilizers, surfactants, thickeners, viscosity modifiers, or vitamins.

The composition may be manufactured by mixing ingredients in a device such as a mixer or extruder, heating the mixture to a temperature of about 175° F. to about 200° F. and continuing to mix for about 10 to about 20 minutes until the mixture becomes colorless. If an opaque composition is desired, the ingredients are mixed without heating.

The composition is useful by itself as a cosmetic for application to the skin. It is also useful as a vehicle or a base for a dye, color pigment, or other cosmetic ingredient to form a cosmetic composition for application to the skin. Such cosmetic compositions or cosmetics include blush, foundation, eyeshadow, and lip color.

The composition may optionally have an active ingredient. The active ingredient may be useful for any medical, therapeutic, or cosmetic purpose known in the art. Examples of such ingredients include, but are not limited, to retinoid and ascorbic acid. The active ingredient may be useful in arresting, ameliorating, diminishing, inhibiting, preventing or treating medical and/or cosmetic conditions of the skin, nail/cuticle, lips or hair. Such conditions include, but are not limited to, acne, psoriasis, eczema, seborrhea, dermatitis, skin and hair fragility, hair loss, hirsutism, rosacea, pruritis, calluses, warts, corns, dry skin, chapped skin, dandruff, skin blemishes, age spots, hyperpigmentation or hypopigmentation, thinning skin, cellulite, stretch marks, dark circles under the eyes, freckles, yellowing, roughness, keratosis, inflammation, discoloration, skin atrophy, wrinkles, lines, hyperplasia, spider veins (telangiectasia), hair loss, bruising, enlarged pores, fibrosis, sunburn, dermatological aging (chronological aging, hormonal aging and/or actinic aging), viral infection, fungal infection, and bacterial infection. An active ingredient may also be useful in enhancing the general health, vitality and appearance of the skin, nail/cuticle, lips and hair.

The composition can have one or more active ingredients that improve the aesthetic and/or cosmetic appearance of skin. Such improvements can be manifested by: reduction in dermatological signs of aging due to, for example, chronological aging, hormonal aging, and photoaging; reduction in skin fragility; reduction in pore size; prevention and/or reversal of loss of collagen and/or elastin; ameliorating the effects of estrogen imbalance; prevention of skin atrophy; prevention and/or reduction in appearance and/or depth of lines and/or wrinkles; improvement in skin tone, radiance, luster, brightness, clarity and/or tautness; prevention, reduction, and amelioration of skin sagging; improvement in skin firmness, thickness, plumpness, texture, suppleness, elasticity and/or softness; minimization of dermatological signs of fatigue and stress; retardation of cellular aging; minimization of skin dryness and/or improvement in skin moisturization; minimization of skin discoloration, including dark eye circles; promotion and/or acceleration of cell turnover; improvement in microcirculation; and decrease and/or prevention in cellulite formation.

EXAMPLES

Example 1

Eyeshadow

| Ingredient | wt % |
|---|---|
| Silica Micro Sphere (MSS 500/3 by Kobo) | 30% |
| Squalane | q.s. |
| Pigment/colorant | 15% to 20% |
| Preservative | 0.5% to 1% |

Example 2

Blush with a Sunscreen

| Ingredient | wt % |
|---|---|
| Silica Micro Sphere (MSS 500/3 by Kobo) | 27% |
| Hydrogenated Polyisobutene | q.s. |
| Octyl Methoxycinnamate | 3% |
| Pigment/colorant | 15% to 20% |
| Titanium Dioxide | 8% |
| Preservative | 0.5% to 1% |

Example 3

Lip Color

| Ingredient | wt % |
| --- | --- |
| Silica Micro Sphere (MSS 500/3 by Kobo) | 30% |
| Squalane | q.s. |
| Pigment/colorant | 15% to 18% |
| Water (Deionized) | 2% |
| Preservative | 0.5% to 1% |

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A gel composition comprising:
   about 10 to about 50 wt % of a powder of porous, spherical silica, the silica powder having a specific gravity of 0.09 to about 0.6; and
   about 35 to about 90 wt % of a non-volatile compound having a viscosity less than about 50 centistokes, wherein the composition has less than about 5 wt % water.

2. The composition of claim 1, wherein the silica powder is present in an amount about 15 to about 45 wt % of the total weight of the composition.

3. The composition of claim 1, wherein the silica powder is present in an amount about 25 wt % to about 35 wt % of the total weight of the composition.

4. The composition of claim 1, wherein the compound is present in an amount about 40 wt % to about 70 wt % of the total weight of the composition.

5. The composition of claim 1, wherein the compound is present in an amount about 45 wt % to about 65 wt % of the total weight of the composition.

6. The composition of claim 1, wherein the silica powder has a specific gravity about 0.2 to about 0.5.

7. The composition of claim 1, wherein the silica powder has a specific gravity about 0.35 to about 0.4.

8. The composition of claim 1, wherein the silica powder is non-fumed.

9. The composition of claim 1, wherein the silica powder has an average particle size about 2 $\mu$m to about 20 $\mu$m.

10. The composition of claim 1, wherein the silica powder has an average particle size about 3 $\mu$m to about 15 $\mu$m.

11. The composition of claim 1, wherein the silica powder has an oil absorption about 100 to about 300 grams of oil per 100 grams of silica.

12. The composition of claim 1, wherein the silica powder has an oil absorption about 120 to about 170 grams of oil per 100 grams of silica.

13. The composition of claim 1, wherein the silica powder has a surface area about 100 m$^2$ to about 1000 m$^2$ per gram of silica powder.

14. The composition of claim 1, wherein the silica powder has a surface area of about 600 m$^2$ to about 800 m$^2$ per gram of silica powder.

15. The composition of claim 1, wherein the compound is a hydrocarbon compound.

16. The composition of claim 15, wherein the hydrocarbon compound is a hydrocarbon oil.

17. The composition of claim 16, wherein the hydrocarbon oil is selected from the group consisting of squalane, liquid paraffin, C$_{12-15}$ alcohol benzoates, hydrogenated polyisobutene, hydrogenated polydecene, and any combinations thereof.

18. The composition of claim 17, wherein the hydrocarbon oil is squalane.

19. The composition of claim 1, wherein the composition is translucent or transparent.

20. The composition of claim 1, wherein the composition has less than about 1 wt % water.

21. The composition of claim 1, wherein the composition has less than about 1 wt % of a volatile compound.

22. The composition of claim 1, wherein the composition is selected from the group consisting of blush, eyeshadow, foundation, and lip color.

23. A gel composition comprising:
   a powder of porous, non-fumed, spherical silica, the silica powder having a specific gravity 0.09 to about 0.6; and
   a non-volatile compound having a viscosity less than about 50 centistokes.

24. A cosmetic composition comprising:
   a gel matrix, wherein the gel matrix consists essentially of about 10 to about 50 wt % of a powder of porous, spherical silica, the silica powder having a specific gravity 0.09 to about 0.6; and
   about 35 to about 90 wt % of a non-volatile compound having a viscosity less than about 50 centistokes.

25. A method for imparting a powdery, non-oily feel to the skin comprising:
   applying to the skin an amount of the composition of claim 1; and
   allowing the composition to set.

26. A method for treating a cosmetic or medical condition of the skin, nail/cuticle, lips or hair comprising applying to the affected area a composition having an effective amount of active ingredient, about 10 to about 50 wt % of a powder of porous, spherical silica with the silica powder having a specific gravity 0.09 to about 0.6, and about 35 to about 90 wt % of a non-volatile compound having a viscosity less than about 50 centistokes, wherein the composition has less than about 5 wt % water.

* * * * *